US007295702B2

(12) United States Patent
Vrhel

(10) Patent No.: US 7,295,702 B2
(45) Date of Patent: Nov. 13, 2007

(54) METHOD FOR SEGMENTING AN IMAGE

(75) Inventor: Michael J. Vrhel, Lebanon, OH (US)

(73) Assignee: Color Savvy Systems Limited, Springboro, OH (US)

( * ) Notice: Subject to any disclaimer, the term of this patent is extended or adjusted under 35 U.S.C. 154(b) by 725 days.

(21) Appl. No.: 10/402,328

(22) Filed: Mar. 28, 2003

(65) Prior Publication Data

US 2003/0198384 A1 Oct. 23, 2003

Related U.S. Application Data

(60) Provisional application No. 60/368,472, filed on Mar. 28, 2002.

(51) Int. Cl.
*G06K 9/00* (2006.01)
*H04N 3/20* (2006.01)

(52) U.S. Cl. ...................................... 382/165
(58) Field of Classification Search ................ 382/110, 382/128, 162, 164, 165, 167, 190, 224, 225, 382/260–264, 253, 283; 345/589, 591, 600–604; 358/515, 526

See application file for complete search history.

(56) References Cited

U.S. PATENT DOCUMENTS

| 4,032,627 | A | 6/1977 | Suchan et al. |
| 6,210,159 | B1 | 4/2001 | Lehmann et al. |
| 6,305,933 | B1 | 10/2001 | Lehmann |
| 6,328,567 | B1 | 12/2001 | Morris et al. |
| 2003/0059090 | A1* | 3/2003 | Zhang et al. ............... 382/110 |
| 2003/0081852 | A1* | 5/2003 | Pohjola ...................... 382/253 |

OTHER PUBLICATIONS

Anderson, M. et al., "A Standard Default Color Space for the Internet-sRGB," Version 1.10 (Nov. 1996).
Therrien, C., *Decision, Estimation, and Classification*, John Wiley & Sons, New York, pp. 217-218 (1989).
Wyszecki, G. et al., *Color Science: Concepts and Methods, Quantitative Data and Formaulae*, John Wiley & Sons, New York, pp. 166-169 (1982).
Pratt, W., *Digital Imaging Processing, Second Edition*, John Wiley & Sons, New York, pp. 171-191 (1991).

\* cited by examiner

*Primary Examiner*—Amir Alavi
(74) *Attorney, Agent, or Firm*—Thompson Hine LLP

(57) ABSTRACT

A method for isolating an element of an image made up of pixels comprising the steps of classifying the pixels into different groups based on the color value of the pixel, blurring the image, locating a pixel in the blurred image that has a predetermined color value corresponding to the element to be isolated, and growing a mask from the located pixel.

20 Claims, 3 Drawing Sheets

METHOD FOR SEGMENTING AN IMAGE

CROSS REFERENCE TO RELATED APPLICATIONS

This application claims priority to Provisional Patent Application Ser. No. 60/368,472 filed Mar. 28, 2002.

FIELD OF INVENTION

This invention relates to a method to identify and isolate a component or feature of a digital image (automated segmentation). More particularly, the invention relates to a method for isolating a feature of an image, such as the teeth, and modifying the isolated feature to show the anticipated effect of a treatment such as whitening or isolating a feature such as hair and modifying it to show the effect of a treatment such as coloring.

SUMMARY OF INVENTION

An image may be captured using any of a variety of methods, but most typically using a standard image capture device (e.g., a digital or web camera or a scanned photographic image might be used), and displayed "live" on a screen. In one embodiment of the invention a "targeting" area may be displayed on the screen, which helps standardize the size (distance from camera) and placement of the image. Once the image is captured, the software analyzes the image, placing each pixel into a color category. All pixels in a category will be part of a particular component or feature of the image, thus isolating and identifying that element.

In one embodiment a digital image of a human face is analyzed to identify pixels that represent the teeth. It identifies the teeth in the image, and then determines their current color and their likely color after a teeth-whitening treatment, which may be determined by a look-up-table or a simple conversion equation.

In another embodiment a digital image of a human head is analyzed to identify pixels that represent hair. It identifies the hair in the image, and then determines its current color. Additional software then uses that information to recommend what coloring products & processes to use to achieve a target color, or to simulate the result when a particular product & process are applied to the existing hair.

One manifestation of the invention is a device for capturing an image and locating a feature of the image using a segmentation program.

Another manifestation of the invention is a device as described above wherein the located feature is modified and redisplayed as part of the original image.

Another manifestation of the invention is a segmentation program for locating a feature of a photographic image.

A more specific manifestation of the invention is a device for capturing an image of a facial feature such as the teeth or hair, locating the facial feature using a segmentation program, modifying the facial feature to display the effect of a change in tooth whiteness or a change in hair color, and displaying the modified image. This device is particularly useful in selling cosmetics.

Another more specific manifestation of the invention is a segmentation program in which a K-means algorithm is used to classify the pixels in an image into color groups.

Another more specific manifestation of the invention is a segmentation program as described immediately above where the original image is blurred to merge smaller segments of the same feature in the image and a pixel representative of the desired feature is located in the blurred image.

Still another manifestation of the invention is a segmentation program in which the pixel identified as described above is grown into a mask using a connection definition.

DETAILED DESCRIPTION

Figure 1:
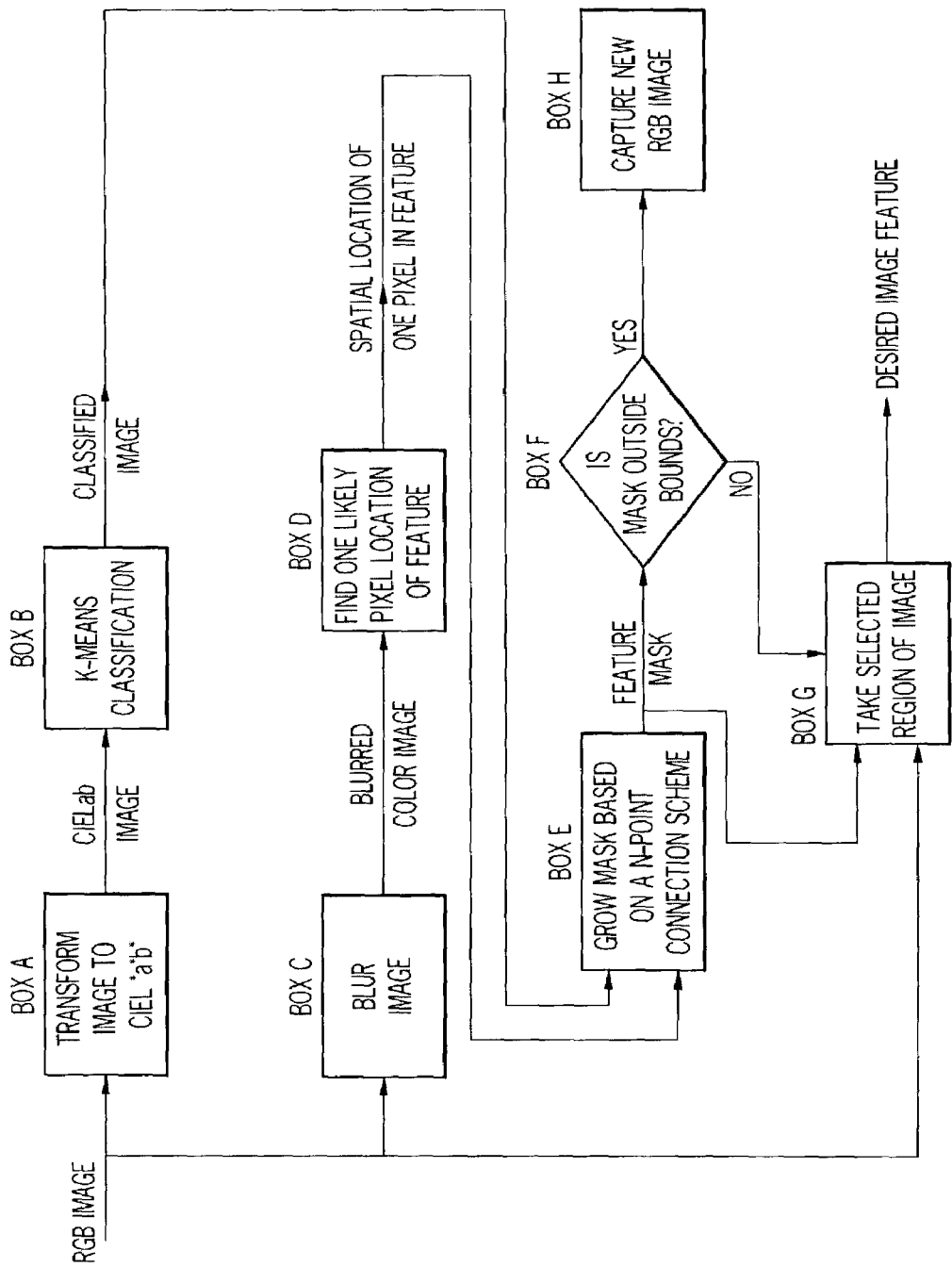
FIG. 1 is a flow chart illustrating a segmenting process in accordance with one embodiment of the invention.

As illustrated in FIG. 1 to conduct the segmentation process the captured image is converted from RGB values to a colorimetric space such as CIELAB. If the RGB values are already in a standard color space (e.g. sRGB (See M. Anderson et. al. , "Proposal for a Standard Default Color Space for the Internet," *IS& /SID 4th Color Imaging Conference*, pp. 238-246, 1996.)), then the transformation is well known and straight-forward. If the RGB values are not in a standard color space, then it is necessary to determine a transformation that will convert the RGB values to CIELAB in a manner that is known in the art. This transformation can be determined once for the capture device that is used, prior to the on-going operation of the device. Details of this operation are given in the block diagram, FIG. 1, and the discussion below.

Figure 2A:
FIG. 2(a) is an image prior to processing.
Figure 2B:
FIG. 2(b) illustrates the image after pixel classification by a K-means algorithm.
Figure 2C:
FIG. 2(c) illustrates the effect of blurring the classified image.
Figure 2D:
FIG. 2(d) illustrates identification of target pixel.
Figure 2E:
FIG. 2(e) is an image of the mask formed using a connection definition, FIG. 2(f) of the segmented feature.

Once, the image is in the CIELAB color space, each pixel in the image is classified (Box B). The method for performing this operation is the K-Means algorithm. For a discussion of this algorithm see C. Therrien, *Decision, Estimation, and Classification*, John Wiley & Sons, N.Y., 1989, pp 217-218. K-Means is a classic iterative pattern recognition algorithm in which a set of data (i.e. the individual pixels) is optimally divided into a set of K classes (i.e. color groups). In this method, an optimization problem is solved to determine the class in which a pixel is contained (i.e. into which color group does the pixel best fit). The selection of the number of categories into which the pixels are classified depends upon the number of distinguishable features in the image or the portion of the image that is the object of the segmentation routine. For the case of teeth, the features may be skin, lips, and teeth (in this case K=3). Additional facial features that are spatially disjointed from the teeth (e.g. moustaches) can be either classified as teeth or non-teeth (e.g., skin or lips) groups. If the feature is incorrectly classified as teeth, the algorithm will keep the teeth and the additional facial feature separate due to their unconnectedness or separation in the image. FIG. 2b illustrates the output of a K-means algorithm (K=5).

After executing the K-means algorithm, there may be several discontinuous or disjointed segments that are contained in the same class or color group. For example teeth and the specular reflection from glossy lips may be within the same class due to the fact that both will appear close to white. If one is only interested in modifying or adjusting the image of the teeth, then it is necessary to separate the teeth pixels from the lip-gloss pixels. If these two sections are not connected, then this separation can be achieved by first identifying a pixel that is within the desired section such as the teeth area. In one embodiment, assuming the desired feature represents the largest section of the image or the targeted area of the image areawise, this identification is achieved by performing a blurring operation on the original RGB image (Box C). The blurred image represents an averaging of the local pixels. Blurring insures that the pixel selected in Box D that is closest in color to the expected color of the desired feature will be in an area of the image that corresponds to the segmented or isolated feature and that the pixel selected is not an aberrant pixel in an area of the image that is not the element to be isolated. The blurring operation has the effect of smearing out the segments that are smaller than the blurring kernel, to the point where no feature including the segment's color is visible. For segments that are larger then the size of the blurring kernel, the color of the segment will remain enabling the determination of the location of one pixel in that segment. The size of the blurring kernel is selected to be smaller than the desired feature. To identify teeth, the expected value might be the whitest pixel. To identify the hair, the expected value might be determined empirically by collecting a set of hair images, blurring them, and computing the average pixel values across the set of images.

The picture shown in FIG. 2 has several regions that are the same color as the element that is the target of the isolation. The desired target is the largest region. To identify a pixel in this region, the portion of the image in the boxed target area is blurred as shown in FIG. 2c using a blurring kernal that is smaller than the desired target. This is the output from Box C in FIG. 1. Assuming for explanation, that this region is green, as the next step in the process, the greenest pixel in the blurred image is selected. This pixel location is output from Box D in FIG. 1.

Having identified the location of one pixel that is within the segment of the class to be separated from the image, to identify the rest of the desired feature, a mask is grown by adding to the identified pixel all pixels that are in this category and connected using a connection definition such as an 8-point connection definition which is well known in the art (Box E). The implementation of the growth algorithm is such that it is relatively insensitive to the connection definition. The details of this growth algorithm are given in the block diagram discussion. This mask is the output of Box E and is illustrated by the image shown in FIG. 2e.

Figure 2F:
FIG. 2 is a series of images that illustrate the photographic effect at different steps of a segmentation process in accordance with one embodiment of the invention.
Figure 3:
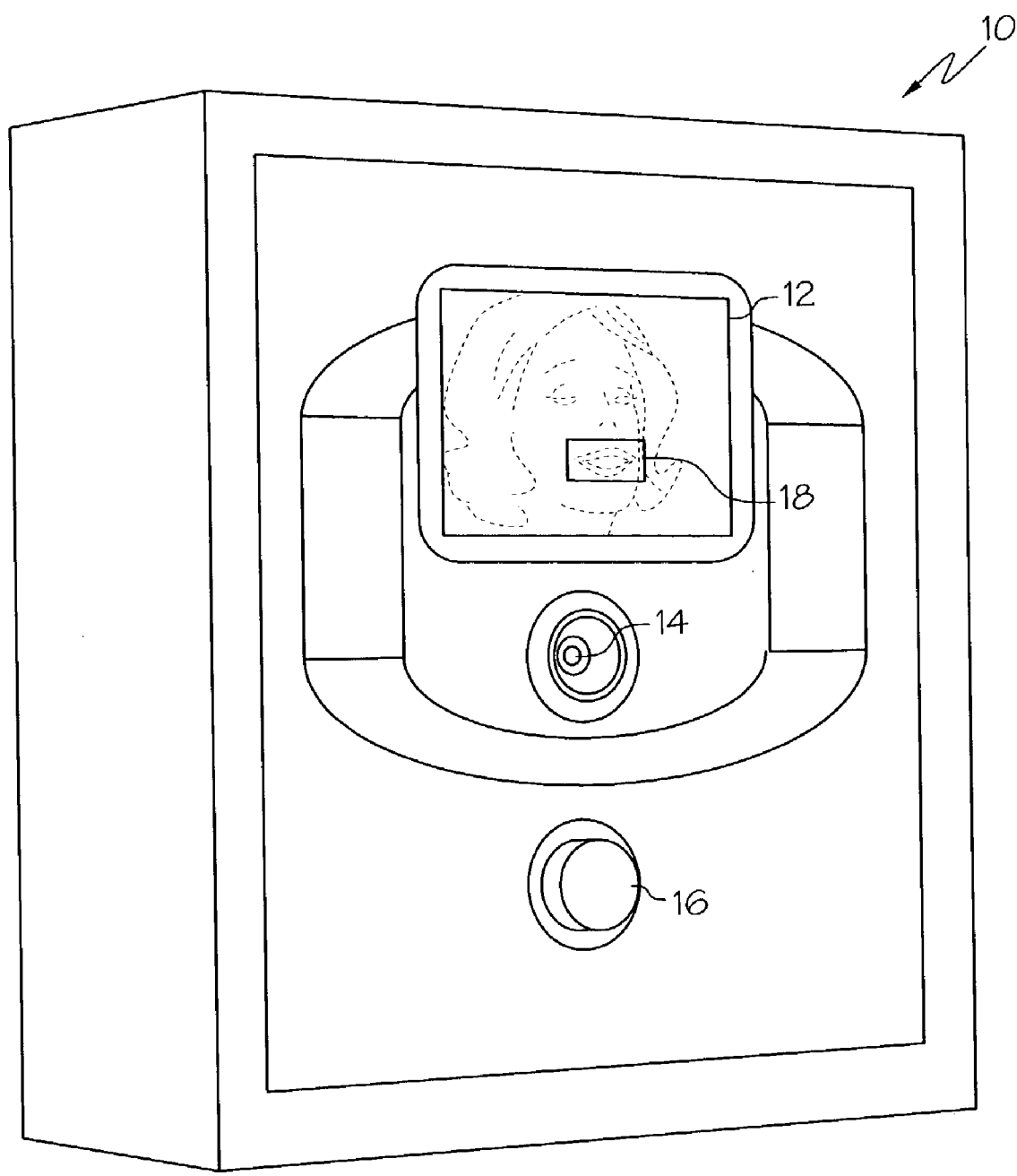
FIG. 3 is an apparatus in accordance with one embodiment of the invention.

The mask defines the area of interest. If the mask reaches any of the edges of the image or is outside of some defined region, then the area of interest was either not found or not entirely within the image. In this case, the user may be instructed to relocate the desired target (e.g., teeth) in the target box 18 as shown in FIG. 3 and discussed below (Box F and Box H). If the mask is good, then the image in the mask area is adjusted as discussed herein. FIG. 2f illustrates the desired segment.

Below are provided the mathematical details of the process.

BOX A

INPUT: RGB image I(x,y).
OUTPUT: Approximate CIELAB image $\hat{F}(I(x,y))$.
PROCESS:

Let the input RGB image be given by I(x,y), where x and y are the spatial location in the image. If the image is contained in a standard RGB color space (e.g. sRGB See M. Anderson et. al. , "Proposal for a Standard Default Color Space for the Internet," *IS& /SID 4th Color Imaging Conference*, pp. 238-246, 1996.), then the conversion from RGB to CIELAB is well defined. If the image is not contained in a standard RGB color space then it is necessary to determine a transformation from RGB to CIELAB. This transformation only needs to be determined one time, but is applied to every captured image. Specifically, the transformation can be determined as follows:

1. The mapping from RGB to CIEXYZ for the input device (likely a web camera or a digital camera) is modeled as a linear system $t = G^T c$ where the RGB pixel value is given by the 3-element vector c, t is the 3-element CIEXYZ value, and G is a 3×3 matrix that is determined as outlined in step 2.

2. The matrix G is determined by measuring a set of N samples with the camera. The CIELAB values of the N samples are determined with a colorimeter. A matrix G is then determined by solving $$G = \arg\left(\min_H \left(\frac{1}{N}\sum_{i=1}^N \|F(H^T c_i) - u_i\|\right)\right)$$

via a modified Newton method where the CIELAB values are given by the vector sequence $\{u_i\}_{i=1}^N$, the measured values from the camera (determined by averaging across a set of pixels) are given by $\{c_i\}_{i=1}^N$, and the mapping from CIEXYZ to CIELAB is given by the function F. See G. Wyszecki, W. S. Stiles, *Color Science: Concepts and Methods, Quantitative Data and Formaulae*, John Wiley & Sons, N.Y., 1982, pp. 166-169. For example, for a Nikon CoolPix 990 camera, G is:

| [0.2818 | 0.1444 | 0.0653 |
|---|---|---|
| 0.1803 | 0.2872 | 0.0382 |
| 0.0404 | 0.0131 | 0.3647] |

3. For simplicity denote the output of this box as $\hat{F}(I(x,y))$.

BOX B

INPUT: Approximate CIELAB image $\hat{F}(I(x,y))$.
OUTPUT: K-Means segmented image K(x,y).

The output CIELAB image $\hat{F}(I(x,y))$ is provided as input to an iterative K-Means algorithm in Box B. Specifically the algorithm is as follows:

1. The bands of the image $\hat{F}(I(x,y))$ (i.e. the 3 color planes (LAB channels) of the image) may be equalized or scaled to provide increased dynamic range, and to maximize the likelihood of being able to differentiate between desired and undesired features. The ideal scaling values are determined experimentally, by testing various scaling values on typical images for a given application.

2. An initial set of K vector values, $k_l$ l=1, . . . , K is selected that may likely differentiate between the desired feature and undesired features in the image. These values should have been determined through experimentation, which involves testing various values on typical images.

3. Each pixel is assigned to one of the K classes. Which class a pixel d is in is determined using $$c = \arg\left(\min_{l}(\|d - k_l\|)\right) l = 1, \ldots, K$$

where $k_l$ is the value of the lth class, and $k_c$ is the class to which pixel d is assigned. In other words, pixel d is assigned to the class closest to it in terms of Euclidean distance.

4. After each pixel has been assigned to a class, update or refine the class values using $$k_l = E\{[d|d \in k_l]\}$$

which are simply the class value means and reassign the pixels based on the refined class values.

5. If the maximum number of iterations has been achieved (a number that is determined experimentally) or no pixels have changed classes, then stop. If not, then go to step 3.

BOX C
INPUT: Approximate CIELAB Image I(x,y).
OUTPUT: Blurred Image B(I(x,y))
PROCESS: See W. K. Pratt, *Digital Image Processing*, John Wiley & Sons, N.Y., 1991, pp 171-191.
The image I(x,y) is blurred in Box C using a convolution process. Mathematically, convolution is given by $$B(I(x, y)) = \int_{-\infty}^{\infty}\int_{-\infty}^{\infty} H(a, b)I(x-a, y, b)\,da\,db$$

where H(a,b) is the blur kernel. The size of the blur kernel should be smaller than the feature that is being detected, and the shape should be symmetric. An example of a symmetric H is given by the equation below, where N is the radius of the blur kernal:

$$H(a,b) = 1/(2N+1)^2 \ \forall -N \le a \le N \ \& \ -N \le b \le N$$

BOX D
INPUT: Blurred Image B(I(x,y))
OUTPUT: Pixel Location $[x_0, y_0]$
PROCESS:
In Box D, a pixel location that is likely in the desired feature is determined. If the color of the expected feature value is given by the three element vector v, then the following algorithm can be used to identify the pixel $$[x_0, y_0] = \arg\left(\min_{[a,b]}(\|B(I(a, b)) - v\|^2)\right)$$

that is simply to find the pixel in the blurred image that is closest to v. The solution to the above optimization problem is achieved by an exhaustive search.

BOX E
INPUT: Pixel Location $[x_0, y_0]$ & K-means image K(i,j).
OUTPUT: Binary Mask Image M(x,y)
PROCESS:
Box E uses the output of the K-Means algorithm (Box B) along with the value $[x_0, y_0]$ (Box D) to create a mask of the desired image feature. The algorithm is as follows:
1. Let there be R rows and C columns in the image.
2. Create a pixel connection definition. One definition that is useful is an 8-point connection. In this case, a pixel d is considered connected to every pixel surrounding it. Mathematically, if d is at location [x,y], then d is connected to the pixels at locations {[x−1, y−1], [x−1,y], [x−1,y+1], [x,y−1], [x,y+1], [x+1,y−1], [x+1,y], [x+1,y+1]}.
3. Create a mask image M(x,y) of size R×C that is zero everywhere.
4. Assign the pixel location $[x_0, y_0]$ with a value 1.
5. Create a temporary mask image $M_T(x,y)$, which is the same as M(x,y).
6. Starting from the spatial locations {[0,0],[R,0],[0,C],[R,C]}, run through the pixels in the images (i.e. step through the pixels in a variety of ways). For a pixel at location [p,q], assign a value 1 to $M_T(p,q)$ if the following conditions are satisfied:
Pixel M(p,q) is connected to a pixel with value 1.
Pixel K(p,q) is in the same class as $K(x_0, y_0)$.
7. Compare the temporary mask $M_T(x,y)$ to the mask M(x,y). Test if any pixels have been reassigned. If no pixels were reassigned, then stop. Otherwise, continue to step 8.
8. Copy the temporary mask $M_T(x,y)$ to the mask M(x,y) and go to step 6.

BOX F
INPUT: Binary Mask Image M(x,y)
OUTPUT: Decision—Was segmentation successful?
PROCESS:
A successful segmentation occurs if the feature is within a bounding box.
If the mask reaches the edge of this box, then the segmentation algorithm failed.
If the mask does not reach the edge of this box, then the segmentation was successful.

BOX G
INPUT: Decision from Box F, Mask Image M(x,y) & Input Image I(x,y).
OUTPUT: Image containing only the segmented feature J(x,y).
PROCESS:
If the output of Box E, M(x,y) is within a pre-defined boundary (tested in Box F), then it is assumed that the desired feature was found. In this case, the mask M(x,y) should be applied to the input image I(x,y) through a point by point operation. Mathematically, this process is:

$$J(x, y) = \begin{cases} I(x, y) & \text{for } M(x, y) = 1 \\ 0 & \text{for } M(x, y) \ne 1 \end{cases}$$

BOX H
INPUT: Decision from Box F
OUTPUT: Restart Image Capture

PROCESS:

If M(x,y) is outside the pre-defined boundary, then the algorithm failed and a new image I(x,y) is captured and the process repeats.

The invention is illustrated in more detail by the following non-limiting example.

EXAMPLE

An image is shown in FIG. 2. FIG. 2a shows a boxed region which indicates the area of interest. FIG. 2b illustrates the output from a K-Means Algorithm in CIELAB space. In this example, 5 classes (K=5) were used. The selected in the coat are clearly selected (they are dark blue here). This image is the typical output of a K-means algorithm. This is the output from BOX B in the flow chart diagram. In this example the object is to select one green portion of the jacket. Within the bounding box, several green portions exist, but the target is the largest connected portion. To determine a pixel in the largest portion, the image is blurred in the bounding box. This is the output from BOX C in the flow chart diagram. The greenest pixel in the blurred image is selected by the X as illustrated. This pixel location is the output from BOX D in the flow chart diagram. The mask image is created from the K-means image and the position marked by the X using the algorithm described for BOX E. The result is then checked to determine if the mask is at the edges of the bounding box. If not, the feature is complete. This is the analysis made by BOX F. In this case, the mask is applied to the input RGB image to obtain the segmented image. This is the output from BOX G. Once the segmentation process is completed, a correction can be applied to the segmented portion (e.g. re-color the teeth to whiten them). The specific nature and amount of correction is predetermined as a function of the process being simulated (e.g. the degree to which teeth can be whitened). The guidelines for the correction can be captured as an equation, algorithm, or look-up table which can be, for example, used with interpolation to map current colors to new colors. Once the correction is applied and the new pixels are determined, the old pixels are replaced with the modified ones.

The segmentation method can be used in a device in which various components are integrated into a cabinet 10 that is designed to hang on a wall or sit on a shelf or counter. The device includes a means for capturing a digital image—typically either a conventional web cam or digital camera 14, a display such as a conventional LCD-type color display 12, a source of light (not shown), and an internal processor that runs the subject software. In its idle state, the display screen can display introductory information (marketing-oriented messages, instructions, or continuous video of images as customers or individuals may see as they pass the camera), and invites the customer to activate the unit by pressing the "go" button 16 on the front of the unit. The go button activates the software. A live image of the subject—as captured by the camera—appears on the screen. The subject is instructed (using on screen prompts) to position himself or herself such that the area of interest (teeth or hair, for example) appears in the on-screen box 18, and to press the "go" button 16 again. Pressing the go button the second time freezes the image on the screen, and begins the segmentation and color analysis. The device segments the image, identifying the pixels of interest, measures the color at multiple points, and calculates an average color value. The device performs calculations based on the initial coloring and displays the result, in this case an image of the customer having whiter teeth or an alternative hair color. After an appropriate delay, the device returns to the idle state.

Having described the invention in detail and by reference to specific embodiments thereof, it will be apparent the numerous modifications and variations are possible without separating from the spirit and scope of the invention.

What is claimed is:

1. A method for isolating an element of an image made up of pixels comprising the steps of classifying the pixels into different groups based on the color value of the pixel, blurring the image, locating a pixel in the blurred image that has a predetermined color value corresponding to the element to be isolated, and growing a mask from the located pixel.

2. The method of claim 1 wherein the step of classifying the pixels into groups is performed using a K-means algorithm.

3. The method of claim 2 wherein the step of growing the mask is performed by adding to the located pixel the pixels in the group in which the located pixel is classified that are spatially connected to the located pixel using a connection algorithm.

4. The method of claim 3 wherein the color of a pixel in the mask is adjusted.

5. The method of claim 4 wherein prior to the step of classifying the image, the image is in RGB color space and is converted to the CIELAB color space.

6. The method of claim 5 wherein the step of converting the image to the CIELAB color space is modeled as a linear system $$t = G^T c$$

where the pixel value is given by the 3-element vector c, t is the 3-element CIEXYZ value, and G is a 3×3 matrix that is determined by solving $$G = \arg\left(\min_H \left(\frac{1}{N} \sum_{i=1}^{N} \|F(H^T c_i) - u_i\|\right)\right)$$

where the CIELAB values are given by the vector sequence $\{u_i\}_{i=1}^{N}$, the RGB values are given by $\{c_i\}_{i=1}^{N}$, and the mapping from CIEXYZ to CIELAB is given by the function F.

7. The method of claim 6 wherein in the step of classifying the pixels includes increasing the dynamic range of the image.

8. The method of claim 7 wherein the image is blurred by using a convolution process including a blur kernel and the blur kernel is smaller than the feature to be isolated.

9. The method of claim 8 wherein the convolution process is given by the equation $$B(I(x, y)) = \int_{-\infty}^{\infty} \int_{-\infty}^{\infty} H(a, b) I(x-a, y, b) \, da \, db$$

where H(a,b) is the blur kernel.

10. The method of claim 9 wherein the function H is given by the equation $$H(a,b) = 1/(2N+1)^2 \; \forall -N \leq a \leq N \; \& \; -N \leq b \leq N$$

where N is the radius of the blur kernel.

11. The method of claim 9 wherein the step of locating the pixel uses the algorithm $$[x_0, y_0] = \arg\left(\min_{[a,b]}(\|B(I(a, b)) - v\|^2)\right)$$

where the color of the expected feature value is given by the three element vector v.

12. The method of claim 2 is wherein the number of groups is 3 to 5.

13. The method of claim 2 wherein the number of groups is sufficient to differentiate the element to be isolated from other elements of the image.

14. The method of claim 2 wherein the step of classifying the pixels includes refining the color value of the different groups based on the group average and reclassifying the pixels in the image based on the refined color values.

15. A computer-readable medium containing instructions for controlling a processor to isolate an element in an image made up of pixels by a method comprising the steps of classifying the pixels into different groups based on the color value of the pixel, blurring the image, locating a pixel in the blurred image that has a predetermined color value corresponding to the element to be isolated, and growing a mask from the located pixel.

16. The medium of claim 15 wherein the step of classifying the pixels into groups is performed using a K-means algorithm.

17. The medium of claim 16 wherein the step of growing the mask is performed by adding to the located pixel the pixels in the group in which the located pixel is classified that are spatially connected to the located pixel using a connection algorithm.

18. The medium of claim 17 wherein the color of a pixel in the mask is adjusted.

19. The medium of claim 18 wherein prior to the step of classifying the image, the image is in RGB color space and is converted to the CIELAB color space.

20. The medium of claim 16 wherein there are 3 to 5 groups.

* * * * *

UNITED STATES PATENT AND TRADEMARK OFFICE
CERTIFICATE OF CORRECTION

PATENT NO. : 7,295,702 B2
APPLICATION NO. : 10/402328
DATED : November 13, 2007
INVENTOR(S) : Michael J. Vrhel Page 1 of 1

It is certified that error appears in the above-identified patent and that said Letters Patent is hereby corrected as shown below:

Column 8

Line 43, beginning of line change equation to read $\{\mathbf{u}_i\}_{i=1}^{N}$

Line 43, after word "by" change equation to read $\{\mathbf{c}_i\}_{i=1}^{N}$.

Line 64, equation should read as follows:

-- $H(a,b) = 1/(2N+1)^2 \quad \forall \; -N \leq a \leq N \;\; -N \leq b \leq N$ --

Signed and Sealed this

Twenty Second Day of April, 2008

JON W. DUDAS
*Director of the United States Patent and Trademark Office*